United States Patent [19]

Forssen

[11] Patent Number: 4,963,363
[45] Date of Patent: Oct. 16, 1990

[54] PHOSPHOLIPID DELIVERY VEHICLE FOR AQUEOUS-INSOLUBLE ACTIVE INGREDIENTS

[75] Inventor: Eric A. Forssen, La Canada, Calif.

[73] Assignee: Vestar, Inc., Pasadena, Calif.

[21] Appl. No.: 346,265

[22] Filed: May 1, 1989

Related U.S. Application Data

[63] Continuation of Ser. No. 7,338, Jan. 27, 1987, abandoned.

[51] Int. Cl.$^5$ .................... A61K 9/133; A61K 45/05; B01J 13/02
[52] U.S. Cl. .................... 424/450; 264/4.1; 264/4.3; 424/420; 428/402.2; 514/245; 514/965
[58] Field of Search ................ 264/4.1, 4.3; 428/402.2; 424/420, 450; 514/965

[56] References Cited

U.S. PATENT DOCUMENTS

| | | | |
|---|---|---|---|
| 3,957,971 | 5/1976 | Oleniacz | 252/DIG. 13 |
| 4,235,871 | 11/1980 | Papahadjopoulos et al. | 264/43 |
| 4,508,703 | 4/1985 | Redziniak et al. | 436/829 X |
| 4,515,736 | 5/1985 | Deamer | 264/4.3 |
| 4,534,899 | 8/1985 | Sears | 260/403 |
| 4,610,868 | 9/1986 | Fountain et al. | 264/4.1 X |
| 4,621,023 | 11/1986 | Redziniak et al. | 428/402.2 |
| 4,708,861 | 11/1987 | Popescu et al. | 264/4.1 X |
| 4,725,442 | 2/1988 | Haynes | 424/450 X |

Primary Examiner—Richard D. Lovering
Attorney, Agent, or Firm—Lyon & Lyon

[57] ABSTRACT

Compositions comprising phospholipid-encapsulated vesicles of active ingredient and triglyceride are described. In a preferred embodiment the vesicles are composed of a hexamethylmelamine active ingredient, with trilaurin or trimyristin as the triglyceride and a mixture of distearoylphosphatidylcholine, distearoylphosphatidylglycerol and cholesterol in the phospholipid outer layer. Preferably the molar ratios of active ingredient: triglyceride: DSPC: CHOL:DSPG will be from about 1:4:2:1:0 to about 1:4:1:1:1. Glycerol may be added to the carrier phase to reduce agglomeration. The composition may be used to deliver otherwise aqueous-insoluble agents to humans or animals to treat, for example, tumors.

18 Claims, 1 Drawing Sheet

PHOSPHOLIPID    LIPID TRIGLYCERIDE    DRUG MOLECULE (HEXAMETHYLMELAMINE)

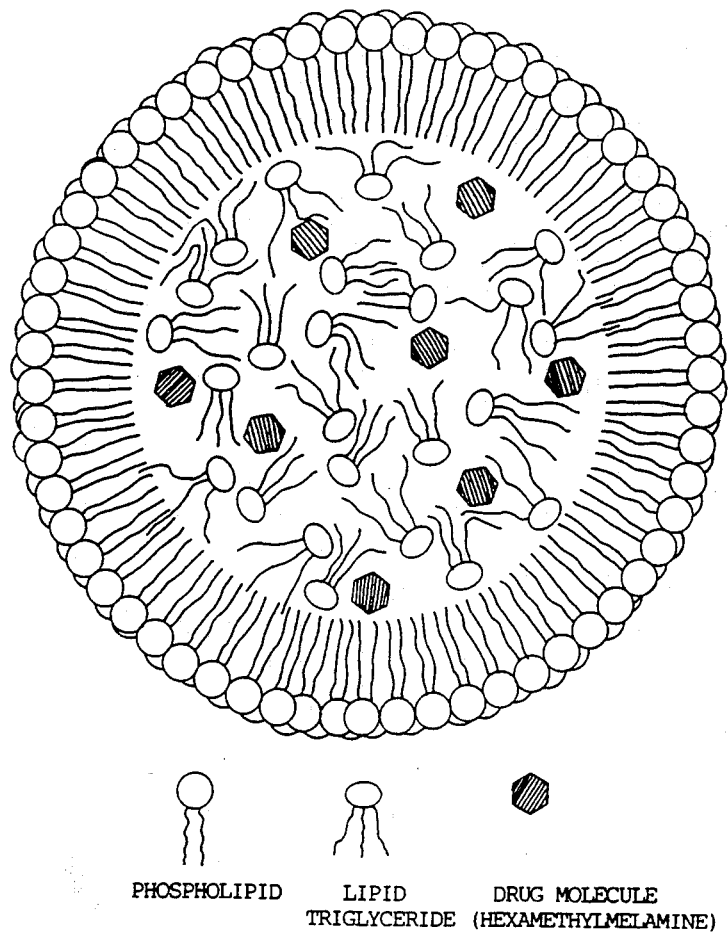

4,963,363

PHOSPHOLIPID DELIVERY VEHICLE FOR AQUEOUS-INSOLUBLE ACTIVE INGREDIENTS

This application is a continuation of application Ser. No. 7,338, filed Jan. 27, 1987 and now abandoned.

FIELD OF INVENTION

This invention relates to phospholipid-encapsulated medicinal agents. It is directed in one aspect to phospholipid-encapsulated hexamethylmelamine. In another aspect it relates to the use of such compositions to deliver medicinal agents to the body, as for example to tumor cells.

BACKGROUND

Although a significant number of substances are known to have antitumor activity, problems have persisted in many cases in developing compositions and methods for safely and effectively delivering such substances to tumor cells. The general toxicity of many anticancer agents prevents their being administered in free form in the body. Many anticancer agents are not sufficiently soluble or stable in the aqueous environment to allow injection or other effective administration. Furthermore, it is frequently useful to control the size of delivery agents in order to achieve targeting to tumor cells or to allow filtration for the purpose of removing deleterious components such as bacteria. It is also important to achieve a composition which, apart from being non-toxic, is biocompatible.

Phospholipid-encapsulated delivery vehicles have been used to overcome such problems in certain cases. It is known, for example, that some aqueous-insoluble drugs can be incorporated into the lipophilic region within the phospholipid bilayer of a liposome to achieve an aqueous-soluble, relatively non-toxic and biocompatible delivery vehicle. Not all aqueous-insoluble materials are susceptible to such a composition, however.

Hexamethylmelamine (HXM) is an example of an anticancer agent which has received only limited use due to its poor aqueous solubility. Oral administration of HXM yields variable absorption and erratic drug concentrations in the plasma. Ames et al., *Cancer Treatment Reports*, Vol. 66, No. 7, pp. 1579-1581 (July 1982). Gentisate and hydrochloride salts of HXM have resulted in severe local irritation upon intravenous administration to humans. Recent attempts to formulate HXM in an intravenously-acceptable preparation have focused on incorporating the drug into fat emulsions, and have achieved HXM concentrations of 2 mg/ml or more. Intraperitoneal formulations have also focused on fat emulsions such as that formed with the oil emulsion vehicle Intralipid (Cutter Laboratories, Berkeley, Calif.), discussed by Wickes et al., in *Cancer Treatment Reports*, Volume 69, No. 6, pp. 657-662 (June 1985). Although such formulations succeed in increasing the concentration of HXM to levels suitable for affecting tumor cells, they do not address the problem of targeting tumor cells specifically through use of phospholipid-encapsulated vesicles of an appropriate size. Nor do they address the problem of sterilization where the medicinal or other component may not be heat-stable since such a preparation can not be sterile filtered.

Accordingly, it is an object of the present invention to provide new compositions for the formulation and delivery of aqueous-insoluble medicinal agents to the body. In one aspect, the invention provides compositions for the formulation and delivery of anticancer agents, including hexamethylmelamine.

It is another object of the present invention to provide methods for manufacturing, sterilization and use of such compositions to deliver medicinal agents to the body, and in particular to tumor cells.

SUMMARY OF THE INVENTION

The present invention involves compositions containing vesicles suitable for delivering medicinal active ingredients to humans or animals. The compositions include vesicles comprising an outer phospholipid coat and an enclosed phase comprising a substantially aqueous-insoluble medicinal active ingredient and a lipid triglyceride component. The vesicles are emulsified in a pharmaceutically acceptable carrier. It is thought that the emulsified vesicles have a roughly spherical outer monolayer of phospholipids with hydrophobic tails of the phospholipid molecules oriented inwardly toward the medicinal active ingredient/lipid triglyceride phase.

A preferred active ingredient is the anticancer agent hexamethylmelamine. Preferred triglycerides with hexamethylmelamine are trimyristoylglycerol (trimyristin) and trilauroylglycerol (trilaurin). The phospholipid outer coating comprises one or more phospholipid materials having from 12 to 20 carbons in the alkyl chains. Distearoylphosphatidylcholine and distearoylphosphatidylglycerol are preferred in the case of the active ingredient hexamethylmelamine. Cholesterol may also be added to the compositions. Preparation of the compositions may be carried out using standard procedures in an appropriate saline or saccharide-based carrier solution. Glycerol may also be added to the aqueous carrier to minimize aggregation of the final compositions.

BRIEF DESCRIPTION OF THE DRAWING

FIG. 1 is a cross-sectional schematic illustration of the theoretical structure of the delivery vehicle of the present invention.

DETAILED DESCRIPTION OF THE INVENTION

As indicated above, the present invention involves the encapsulation and improved delivery of aqueous-insoluble active ingredients, and in particular insoluble anticancer agents such as hexamethylmelamine, in phospholipid vesicles. The present compositions may be used in some cases where other delivery vehicles, such as liposomes, are not satisfactory.

Hexamethylmelamine (HXM), or 2,4,6-Tris(dimethylamino)-s-triazine, is an anticancer compound that is very similar structurally to the alkylating agent triethylenemelamine. Its structure is as follows:

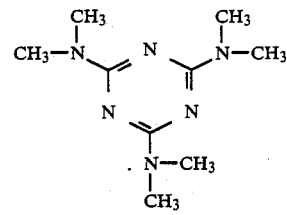

As discussed above, the poor aqueous solubility of HXM has hindered its usefulness in anticancer therapy. Investigations relating to the present invention have shown that improved solubilization of HXM in a phospholipid vesicle may be achieved with the present delivery vehicles as compared to liposomal compositions.

The present compositions are thought to have a structure as shown in FIG. 1 in cross-section. The delivery vehicle may be roughly spherical in shape. The inner phase of the delivery vehicle includes the active ingredient dissolved in a lipid triacylglycerol (triglyceride). Because this inner phase is essentially lipophilic, it will form a stable association with an encapsulating monolayer of phospholipids. The hydrophilic nature of the outer surface of the encapsulating layer allows aqueous and in vivo solubilization, and may achieve other advantages associated with liposomal structures (including biocompatibility, isolation of active ingredient toxicity and targeting of tumor cells).

It is necessary to utilize an appropriate lipid triglyceride in order to achieve a satisfactory delivery vehicle. A given active ingredient may be soluble in a number of triglycerides, or it may be made soluble by, for example, altering pH or ionic strength of the mixture or by complexing the active ingredient with a second lipid-soluble agent. Nevertheless, not all lipid triglycerides that can solubilize a given active ingredient will necessarily be compatible with a stable phospholipid emulsion. For example, fully-saturated long chain triglycerides such as tripalmitin and tristearin solubilize HXM upon heating but tend to form a hard waxy composition upon cooling that cannot be satisfactorily emulsified with the phospholipids tested. Conversely, the long unsaturated alkyl chain in the triglyceride triolein will allow an emulsion with phospholipids, but the triglyceride is ineffective at solubilizing HXM. Shorter-chain triglycerides such as triacetin and tributyrin poorly solubilize HXM and do not form stable emulsions in the compositions tested.

In the case of the active ingredient HXM, it is preferred that the lipid triglycerides trimyristin or trilaurin be used. These triglycerides will solubilize the active ingredient and are able to form stable emulsions. Other appropriate triglycerides, including those having mixed alkyl chains, may also be useful and may be ascertained through relatively routine experimentation given the disclosure of the present invention. The choice of an appropriate triglyceride will, of course, depend on a number of factors including the type and desired concentration of the active ingredient, the type of phospholipid or phospholipid mixture being used, and the nature of other components in the mixture in which the composition is being formulated. Therefore, the particular triglycerides disclosed or preferred herein are not intended to limit the scope of the present invention, but rather to exemplify embodiments which have been shown to be effective.

The active ingredient to be used herein will typically be one or more compounds which are insoluble in aqueous media or which require enhanced solubilization to achieve useful concentration. With respect to HXM, for example, solubility of the free drug in saline solution has been reported to be as low as 0.070 mg/ml (Wickes et al., *Cancer Treatment Reports,* Volume 69, No. 6, pp. 657–662 (June 1985)) and as high as 0.20 mg/ml in water (Ames et al., *Cancer Treatment Reports,* Volume 66, No. 7, pp. 1579–1581 (July 1982)). A desirable concentration would exceed 1.0 mg/ml measured with respect to HXM content.

Although the active ingredients useful in the present invention will typically be agents that are difficult to solubilize in aqueous media, this need not necessarily be the case. So long as the active ingredient can be made compatible with the triglyceride phase, and so long as it is desirable to encapsulate the ingredient in a phospholipid monolayer, the present invention may yield a useful delivery vehicle. As discussed above, modifications to the pH or ionic strength of the mixture, or modifications to the active ingredient such as complexation, may be employed to render the ingredient triglyceride-soluble. Similar modifications may be made to allow formation of a stable phospholipid vesicle.

The outer phospholipid coating may be composed of a range of phospholipids including neutral phospholipids such as phosphatidylcholines and phosphatidylethanolamines, as well as ionic phospholipids such as phosphatidylglycerols and phosphatidylserines. Preferred phospholipids are those having from 12 to 20 carbons in their alkyl side chains. Cholesterol may also be added as a component of the outer layer and is preferred in many cases.

Distearoylphosphatidylcholine is a particularly preferred phospholipid with the active ingredient HXM and the inner phase triglyceride trilaurin. The anion distearoylphosphatidylglycerol may also be added to yield a successful composition. Cholesterol is a preferred component in the outer coating. The molar ratio of ingredients in such a HXM composition will preferably range as follows:

| | |
|---|---|
| HXM: | 1 |
| Distearoylphosphatidylcholine: | 2–1 |
| Cholesterol: | 1 |
| Distearoylphosphatidylglycerol: | 0–1 |
| Trilaurin: | 4 |

The formation of the emulsified delivery vehicles may be achieved in a saline solution, as for example a 0.9% solution of sodium chloride in water, or in a saccharide or disaccharide solution, such as 5% dextrose or 9% lactose in water. In addition, it is often preferred to add glycerol to the mixture in a concentration of about 100 mM in order to reduce or eliminate any adverse tendency toward aggregation of the vesicles. Formation of the vesicles may be achieved using standard sonication techniques. Such is the case with the HXM compositions described herein.

Non-solubilized material may be removed from the mixture by centrifugation. Further purification may include filtration, for example, through a 5-micrometer filter needle to ascertain syringeability, and through a 0.45 and/or 0.22-micrometer filter to remove, e.g., bacterial contaminants. The final delivery vehicle vesicles will preferably be smaller than 100 nm in diameter, and preferably in the range 40–75 nm in diameter.

The following examples demonstrate the preparation and characterization of one form of the delivery vehicles of the present invention, and are not intended to limit the scope of the invention as set forth here and in the claims. Example 2 is given to compare one of the present compositions with a liposome-type delivery vehicle tested for use with HXM.

EXAMPLE 1

Preparation of a Hexamethylmelamine-Trilaurin Delivery Vehicle Encapsulated With Phospholipid.

Hexamethylmelamine was supplied by the National Cancer Institute, compound NSC-13875, lot number H739646. Solubility tests were run for HXM in a number of pure triglycerides and it was determined that HXM was highly soluble (more than 50 mg/ml) in tributyrin, trihexanoin, tricaprylin, trilaurin and tripalmitin (Sigma Chemical Co., St. Louis, Mo.). Emulsions of HXM were formed by heating a measured quantity of the triglyceride to a liquid state and adding with stirring measured quantities of HXM, phospholipid (Avanti Biochemicals, Birmingham, Ala.), cholesterol (Sigma) and, finally, the aqueous solution phase. The solution was then sonicated under an inert atmosphere using a probe type sonicator (Sonics and Materials, Model VCS-500, Danbury, Conn.). The sample was then centrifuged at 750 g for ten minutes and the amount of precipitate estimated. An alternate composition was sought if the total precipitation was greater than about 20% of the starting material. Preferably, the precipitate fraction would be less than 10%.

Following filtration of the emulsion of delivery vehicles through a 5-micrometer filter needle to verify syringe-ability, the samples were filtered through 0.45 and/or 0.22 micrometer microfilters. They were then analyzed for total HXM concentration and for evidence of any HXM decomposition using thin layer chromatography on silica gel 60 plates (Merck), high pressure liquid chromatography and/or UV/visible spectroscopy using a Perkin-Elmer Lamda 3B spectrophotometer.

The results of such procedures are summarized in Table 1.

An alternate procedure for formulating the present compositions, useful especially for small batches, involves dissolving each desired component in an organic solvent such as chloroform, mixing appropriate volumes of each chloroform solution, evaporating the chloroform under vacuum to obtain a lipid-drug-triglyceride film, and then adding this film to the appropriate aqueous phase as discussed above.

EXAMPLE 2

Incorporation of Hexamethylmelamine Into Liposomal Delivery Vehicles

By way of comparison, attempts were made to incorporate HXM into the intra-bilayer phospholipid region of a liposome without use of any triglyceride. Appropriate proportions of HXM, phospholipid and cholesterol were dissolved in an organic solvent such as chloroform (distearoylphosphatidylglycerol was dissolved in 1:1 methanol:chloroform and then mixed with the chloroform solution). The solvent was then removed under reduced pressure to yield a lipid-drug film. This film was then mixed and sonicated as above in an appropriate aqueous solvent to yield small unilamellar liposomal vesicles. As above, the addition of 100 mM glycerol prevented agglomeration in some instances. Following centrifugation, the liposomes were filtered and analyzed for HXM concentrations in aqueous solution.

Results of these tests showed that addition of the anion distearoylphosphatidylglycerol increased the

TABLE 1

| Composition of Mixture[1] | Triglyceride | Aqueous Phase | % Precipitation[2] | Final HXM Concentration[3] |
|---|---|---|---|---|
| HXM:DSPC:CHOL:DSPG:TRI | | | | |
| 1:3:1:0:3 | Tributyrin | Lactose, 9% Glycerol, 100 mM | 10% | 0.61,0.70(n = 2) |
| 1:2:1:0:4 | Tripalmitin | Dextrose, 5% | 100% | — |
| 1:2:1:0:4 | Tripalmitin | Dextrose, 5% Glycerol, 100 mM | 100% | — |
| 1:2:1:1:4 | Tripalmitin | Dextrose, 5% | 100% | — |
| 1:2:1:1:4 | Tripalmitin | Dextrose, 5% Glycerol, 100 mM | 100% | — |
| 1:2:1:0:4 | Trilaurin | NaCl, 0.9% | 10% | — |
| 1:2:1:0:4 | Trilaurin | NaCl, 0.9% Glycerol, 100 mM | 5% | 2.5 |
| 1:2:1:0:4 | Trilaurin | Dextrose, 5% | 10% | — |
| 1:2:1:0:4 | Trilaurin | Dextrose, 5% Glycerol, 100 mM | 5% | 3.0 |
| 1:1:1:1:4 | Trilaurin | NaCl, 0.9% | 10% | — |
| 1:1:1:1:4 | Trilaurin | NaCl, 0.9% Glycerol, 100 mM | >5% | 3.0,2.2(n = 1) |
| 1:1:1:1:4 | Trilaurin | Dextrose, 5% | 10% | — |
| 1:1:1:1:4 | Trilaurin | Dextrose, 5% Glycero;, 100 mM | >5% | 3.1,2.2(n = 1) |

[1] Molar ratios. Abbreviations: HXM — hexamethylmelamine; DSPC — distearoylphosphatidyl-choline; CHOL — cholesterol; DSPG — distearoylphosphatidlglycerol; TRI — triglyceride
[2] Approximate percent precipitation of components following centrifugation at 750 G for ten minutes
[3] Concentration of HXM in mg/ml, after filtration through 5.0-micrometer and 0.45-micromete filters.

Table 1 demonstrates that useful concentrations of HXM in aqueous solution may be achieved using the compositions of the present invention. Preferred formulations use tripalmitin in the inner phase, and 100 mM glycerol dissolved in the aqueous phase. Analysis using UV/visible spectroscopy of the four trilaurin compositions tested for final HXM concentration showed no noticeable difference from the starting drug. Thin layer chromatography was also consistent with intact HXM in these cases. A repeated UV/visible spectroscopic analysis after 24 hours indicated diminished absorbance at 227 nm, suggesting a decrease in aqueous HXM from about 3.0 to 2.2 mg/ml. The later spectra were consistent with intact HXM.

amount of membrane-incorporated HXM by promoting partitioning of the drug into the lipid phase. However, the final concentration of HXM achieved did not in such cases reach the desired level of at least 1.0 mg/ml. Based on these results, the desirability of the alternative aqueous solubilization vehicles disclosed herein becomes clear.

What is claimed is:

1. A composition suitable for the delivery of an active ingredient comprising monolayer vesicles of about 30 to about 200 nanometers in a pharmaceutically acceptable carrier, the vesicles comprising an active ingredient in mixture with a triglyceride selected from the group consisting of trimyristoylglycerol and trilauroylglycerol, and an encapsulating consisting of a monolayer which comprises a phospholipid material.

2. The composition of claim 1 wherein the encapsulating layer includes cholesterol.

3. The composition of claim 1 wherein the active ingredient is substantially aqueous-insoluble.

4. The composition of claim 1 wherein the phospholipid material is selected from the group of phospholipids having alkyl side chains of from 12 to 20 carbons in length.

5. The composition of claim 4 wherein the phospholipid material includes an anionic phospholipid component.

6. The composition of claim 1 wherein the phospholipid material comprises a mixture of dialkoylphosphatidylcholine and dialkoylphosphatidylglycerol compounds having alkyl side chains of from 12 to 20 carbons in length.

7. The composition of claim 6 wherein the encapsulating layer includes distearoylphosphatidylcholine, distearoylphosphatidylglycerol and cholesterol.

8. The composition of claim 1 wherein the carrier is an aqueous saline solution, an aqueous monosaccharide solution or an aqueous disaccharide solution.

9. The composition of claim 1 wherein the carrier includes glycerol.

10. A composition suitable for the delivery of a hexamethylmelamine active ingredient comprising monolayer vesicles of about 30 to about 200 nanometers in a pharmaceutically acceptable carrier, the vesicles comprising hexamethylmelamine in mixture with a triglyceride selected from the group consisting of trimyristoylglycerol and trilauroylglycerol, and an encapsulating layer consisting of a monolayer which comprises a phospholipid material.

11. The composition of claim 10 wherein the phospholipid material includes an anionic phospholipid component.

12. The composition of claim 10 wherein the phospholipid material comprises a mixture of dialkoylphosphatidylcholine and dialkoylphosphatidylglycerol compounds having from 12 to 20 carbons in length.

13. The composition of claim 12 wherein the encapsulating layer includes distearoylphosphatidylcholine, distearoylphosphatidylglycerol and cholesterol.

14. The composition of claim 10 wherein the carrier includes glycerol and is an aqueous saline solution, an aqueous monosaccharide solution or an aqueous disaccharide solution.

15. A method for treating neoplastic tumors in a human body comprising parenterally administering multiple doses of the composition claimed in claims 1 or 10.

16. The method of claim 15 wherein the administration is by intravenous injection.

17. A method of making a composition suitable for the delivery of an active ingredient comprising the steps of:

(1) solubilizing an active ingredient with a mixture consisting essentially of a triglyceride selected from the group consisting of trimyristoylglycerol and trilauroylglycerol, a phospholipid material and a pharmaceutically acceptable carrier;

(2) forming vesicles containing the active ingredient; and (3) removing undesirable materials from the resulting composition, wherein said vesicles are monolayer vesicles comprising an encapsulating monolayer of phospholipid material.

18. The method of claim 17 wherein said vesicles have a size of about 30 to about 200 nanometers.

* * * * *